United States Patent [19]

Yoshimura et al.

[11] Patent Number: 4,529,697

[45] Date of Patent: Jul. 16, 1985

[54] PROCESS FOR PRODUCING L-GLUTAMIC ACID BY FERMENTATION

[75] Inventors: Minoru Yoshimura; Yosuke Koyama, both of Kawasaki; Koichi Goto, Yokohama; Sumio Inoue, Yokohama; Shigeho Ikeda, Yokohama; Hiroe Yoshii, Yokohama, all of Japan

[73] Assignee: Ajinomoto Co., Inc., Tokyo, Japan

[21] Appl. No.: 475,648

[22] Filed: Mar. 15, 1983

[30] Foreign Application Priority Data

Mar. 15, 1982 [JP] Japan ................................ 57-41411

[51] Int. Cl.³ ...................... C12P 13/14; C12N 15/00; C12N 1/20; C12R 1/13; C12R 1/15

[52] U.S. Cl. ................................ 435/110; 435/172.1; 435/840; 435/843; 435/253

[58] Field of Search .................... 435/110, 172.1, 840, 435/843

[56] References Cited

U.S. PATENT DOCUMENTS

| | | | |
|---|---|---|---|
| 4,334,020 | 6/1982 | Nakazawa et al. | 435/110 |
| 4,347,317 | 8/1982 | Yoshimura et al. | 435/110 |
| 4,389,483 | 6/1983 | Hiraga et al. | 435/110 |

*Primary Examiner*—Lionel M. Shapiro
*Attorney, Agent, or Firm*—Oblon, Fisher, Spivak, McClelland & Maier

[57] ABSTRACT

A process for producing L-glutamic acid by fermentation is disclosed, which process comprises culturing aerobically in a culture medium a mutant of the genus Brevibacterium or Corynebacterium which has an increased superoxide dismutase activity and is capable of producing L-glutamic acid in the culture medium and recovering the L-glutamic acid. The yield of L-glutamic acid can be increased by using the aforementioned mutants.

9 Claims, No Drawings

PROCESS FOR PRODUCING L-GLUTAMIC ACID BY FERMENTATION

BACKGROUND OF THE INVENTION

1. Field of the Invention

The present invention relates to a process for producing L-glutamic acid by fermentation.

2. Description of the Prior Art

L-glutamic acid, in the form of the monosodium salt, has been used as a seasoning and has previously been produced by a fermentation process in which wild strains or artificial mutants of L-glutamic acid-producing bacteria, especially of the genus Brevibacterium or Corynebacterium, are used.

Currently, various artifical mutants of the genus Brevibacterium or Corynebacterium capable of producing L-glutamic acid are known. Examples of such artificial mutants are mutants requiring L-arginine, L-histidine, pyrimidine, hypoxanthine, glycerol, chemical compounds having a disufide linkage, or an unsaturated fatty acid such as oleic acid (as described in Japanese Published Examined patent application Nos. 507/1967, 508/1967, 509/1967, 27390/1970, 27391/1970, 19632/1975, 33997/1976, 2998/1977, 6233/1978, 6234/1978, and 8798/1978); mutants resistant to chloramphenicol, streptomycin, chlortetracycline, S-(2-aminoethyl)cystein, monofluoracetic acid, fluorocitric acid, ketomalonic acid, α-amino-β-hydroxyvaleric acid, DL-threonine hydroxamate, 2-amino-3-phosphopropionic acid, 5-aminolevulinic acid, glutamic acid analogues, benzopyrone, naphthoquinone, or 2,6-pyridinedicarboxylic acid or to inhibitors of the bacterial respiratory system such as malonic acid, $NaN_3$, KCN, sodium arsenite, 2,4-dinitrophenol, hydroxyamine, and guanidine (as described in Japanese Published Unexamined patent application Nos. 4398/1966, 126877/1975, 38088/1977, 89085/1979, 21763/1980, 21764/1980, 124492/1980, 1889/1981, 35981/1981, 39778/1981, and 48890/1981); mutants sensitive to N-palmitoyl glutamic acid, lysozyme, or to a temperature of more than 34° C. (as described in Japanese Published Unexamined patent application Nos. 64486/1975, 32193/1978, 66687/1977, 122794/1979, and 114293/1980); and a mutant having reduced activity with respect to pyruvic acid dehydrogenase (as described in Japanese Published Unexamined patent application No. 21762/1980). However, because of the continued desirability of increased L-glutamic acid production, processes for the increased production of L-glutamic continue to be sought.

SUMMARY OF THE INVENTION

It is an object of the present invention to provide a method of increasing the production of L-glutamic acid.

This and other objects of the invention as will hereinafter become more readily apparent have been accomplished by providing a process for producing L-glutamic acid by fermentation, which process comprises culturing aerobically in a culture medium a mutant of the species Brevibacterium or Cornyebacterium which has increased superoxide dismutase activity over that present in the parent strain from which said mutant is derived and which is capable of producing L-glutamic acid in the culture medium, and recovering the L-glutamic acid from the culture medium.

DETAILED DESCRIPTION OF THE PREFERRED EMBODIMENTS

It has now been found (and this discovery forms the basis of the present invention) that the production of L-glutamic acid can be increased when the superoxide dismutase activity of an L-glutamic acid-producing microorganic strain is reinforced or increased over that present normally, and that the mutants having increased superoxide dismutase activity can be obtained from among the artificial mutants resistant to a superoxide propagator, i.e., a chemical agent which produces a superoxide.

The microorganisms employed in the process of the present invention are mutants which belong to the genus Brevibacterium or Corynebacterium, have an increased superoxide dismutase activity, and have an ability to produce L-glutamic acid. Preferably the mutant employed in the process of the present invention belongs to the species *Brevibacterium lactofermentum, Brevibacterium flavum, Corynebacterium glutamicum* or *Corynebacterium acetoacidophilum*. Preferable examples of such mutants of the present invention include the following:

*Brevibacterium lactofermentum:* AJ 11796 FERM-P 6402, FERM BP-251, ($DM^r$, SOD increased)

*Corynebacterium glutamicum:* AJ 11801 FERM-P 6398, FERM BP-250, ($MV^r$, SOD increased)

where the stated terms have the following meanings:

SOD increased: having an increased superoxide dismutase activity over that present in the unmutated parent strain $DM^r$: resistance to Daunomycin, and $MV^r$: resistance to Methylviologen.

The AJ numbers are internal reference numbers of the present inventors.

The mutants identified above by FERM-BP numbers were originally deposited on Mar. 1, 1982, at the Fermentation Research Institute, Agency of Industrial Science and Technology, Ministry of International Trade and Industry (FRI), 1-3 Higashi 1-chome, Yatabemachi, Tsukuba-gun, Ibaragi-ken 305, Japan, at which time they received the indicated FERM-P numbers, and these deposits were converted to the FERM-BP deposit number under the Budapest Treaty on Feb. 3, 1983. FRI acquired the status of an International Depositary Authority as of May 1, 1981.

The mutants indicated above were induced from parent strains of the genus Brevibacterium or Corynebacterium by a conventional method. The first step of the induction is to mutate the parent strain with a suitable chemical mutagen such as N-methyl-N'-nitro-N-nitrosoguanidine (hereinafter referred to as NG) or nitrous acid or by irradiation with ultraviolet light.

The second step is to select a mutant resistant to a superoxide propagator by picking up the colonies grown on plates of nutrient agar medium containing an amount of a superoxide propagator which inhibits the growth of the parent strain. This amount can be easily be determined by simple experimentation. Finally, the mutants are evaluated for L-glutamic acid production according to a standard method which measures L-glutamic acid present in the culture medium.

The mutants FERM BP-251 and FERM BP-250 have the same general characteristics as their parent strain, i.e., ATCC 13869 and ATCC 13032, and additionally have increased superoxide dismutase activity and resistance to Daunomycin or Methylviologen, respectively.

As the parent strains, any wild strain capable of producing L-glutamic acid of the genus Brevibacterium or Corynebacterium can be employed. The preferred wild strains are coryne-form glutamic acid-producing bacteria and include the following examples:
Brevibacterium lactofermentum: ATCC 13869
Brevibacterium flavum: ATCC 14067
Brevibacterium divaricatum: ATCC 14020
Brevibacterium saccharoliticum: ATCC 14066
Corynebacterium glutamicum: ATCC 13032
Corynebacterium acetoacidophilum: ATCC 13870

As another type of the parent strain, mutants of the genus Brevibacterium or Corynebacterium which are induced from wild strains as stated above and have biological characteristics known to be effective for production of L-glutamic acid, such as resistance to fluoromalonic acid, fluorocitric acid, ketomalonic acid, and 2,6-puridinedicarboxylic acid and sensitivity to lysozyme and N-palmitoylglutamate, are preferably used.

These characteristics, useful for the production of L-glutamic acid, can be imparted prior to or after giving to the wild strains the resistance to the antibiotics.

The superoxide radical is one of the active forms of oxygens and is represented by $O_2-$, $.O_2-$ or $.O_2H$. This radical is generated in vivo when oxygen ($O_2$) is reduced in an oxidation reaction catalysed by Xanthineoxidase (EC 1,2,3,2) or in an autooxidation reaction of a cell's components. It is well known that the superoxide radical reacts with unsaturated fatty acids to produce a superoxide of the fatty acid. The superoxide thus produced is harmful to living cells and causes an undesirable drop in the various biochemical activities of the living cells.

Similarly, a superoxide of an unsaturated fatty acid is generated in cells of L-glutamic acid-producing microorganisms which have been cultured aerobically, i.e., under oxidative condition, and which are producing L-glutamic acid in the culture medium. Thereby, the activity of the cells, such as their ability to produce L-glutamic acid, gradually drops with time when the cells are cultured for a long time.

A superoxide propagator is a chemical agent which produces a superoxide harmful to living cells and usually inhibits the growth of microorganisms. Superoxide propagators include the following: Methylvioloben, Nitrofurantoin, Vitamin K, Morphine, Adriamycin, Mitomuycin C. Daunomycin, and Bleomycin.

Superoxide dismutase (EC 1,15,1,1) can catalyze the following reaction:

$$2 O_2-.+2 H^+ \rightarrow H_2O_2+O_2$$

It is known that a superoxide dismutase may defend a living body from disruption caused by an active oxygen such as a superoxide (Fridovich, Ann. Rev. Biochem., 44, 147-159 (1975)).

Accordingly, the mutants of the present invention having an increased superoxide dismutase activity will maintain a cell's activity under oxidative condition for a longer time, and thereby can produce a larger amount of L-glutamic acid than their parent strains.

Conveniently the process of the present invention also includes recovering the L-glutamic acid which accumulates in the culture medium.

The method by which the mutants of the present invention can be induced, the typical degree of resistance to the superoxide propagator obtained, and typical activities of the superoxide dismutase are exemplified in the following Experiments 1, 2 and 3, which are not intended to be limiting of the present invention unless otherwise specified.

EXPERIMENT 1

Cells of the known microorganic strain

Brevibacterium lactofermentum ATCC 13869 grown on a slant of bouillion agar medium were scraped off and suspended in sterilized water containing 150 μg/ml NG, and the suspension was allowed to stand at 30° C. for 20 minutes. The microbal cells thus treated were washed with phosphate buffer solution and then inoculated on agar plates, the composition of which is given in Table 1, further containing 3 μg/ml Daunomycin.

TABLE 1

| Composition of the agar medium (pH 7.0) | |
|---|---|
| Component | Conc. |
| Yeast extract | 1.0 g/dl |
| Peptone | 1.0 g/dl |
| NaCl | 0.5 g/dl |
| Agar | 2.0 g/dl |

The plates were then incubated at 30° C. for 2 to 4 days until colonies developed on the plates. The colonies were collected as the Daunomycin-resistant mutants and were evaluated for producing L-glutamic acid according to a standard method.

It was found that mutants which have an increased activity with respect to superoxide dismutase and provide greater production of L-glutamic acid than the parent strain were obtained with high frequency.

From among these mutants, B. lactofermentum AJ 11796 FERM BP-251, which can produce more L-glutamic acid than any other mutant, was selected. The mutants resistant to Methylviologen of the present invention were obtained in a similar manner to that described above.

EXPERIMENT 2

Four-milliliter portions of an aqueous GM medium having the composition specified in Table 2, some of which contained the definite amount of the superoxide propagator specified in Table 3, were poured into small test tubes and heated for sterilization.

TABLE 2

| Composition of GM medium | | | |
|---|---|---|---|
| Component | Conc. | Component | Conc. |
| Glucose | 0.5 g/dl | $CaCl_2$ | 0.1 mg/dl |
| Ammonium Sulfate | 0.15 g/dl | $MnCl_2.4H_2O$ | 0.36 mg/dl |
| Urea | 0.15 g/dl | $Na_2B_4O_7.10H_2O$ | 0.44 mg/dl |
| $K_2HPO_4$ | 0.1 g/dl | $CuSO_4.5H_2O$ | 1.95 mg/dl |
| $KH_2PO_4$ | 0.3 g/dl | $ZnSO_4.7H_2O$ | 44 mg/dl |
| $MgSO_4.7H_2O$ | 0.01 g/dl | Biotin | 3 μg/ml |
| $FeCl_3.6H_2O$ | 4.85 g/dl | Thiamine HCl | 10 μg/ml |
| $(NH_4)Mo_7O_{24}.4H_2O$ | 0.18 g/dl | | |

Each strain to be tested was washed with GM medium and suspended in GM medium to prepare the cell suspension of which the optical density (at 26-times dilution) at 562 nm was 0.1. A sample (0.1 ml) of cell suspension was then transferred from each batch of GM medium and placed in the test tubes. Cultivation was carried out at 30° C. for 30 hours with shaking. After the cultivation, the degree of growth of each strain was determined by measuring optical density at 562 nm of a 26-times diluted solution of the resultant culture broth, and the results obtained are shown in Table 3.

TABLE 3

| Superoxide propagator | Conc. (μg/ml) | Degree of resistance | | | |
|---|---|---|---|---|---|
| | | ATCC 13969 | AJ 11796 | ATCC 13032 | AJ 11801 |
| Daunomycin | 0.0 | 100 | 100 | | |
| | 0.5 | 50 | 80 | | |
| | 1.0 | 30 | 60 | | |
| | 2.0 | 0 | 30 | | |
| | 3.0 | 0 | 10 | | |
| Methyl-viologen | 0 | | | 100 | 100 |
| | 50 | | | 59 | 85 |
| | 100 | | | 20 | 63 |
| | 150 | | | 10 | 45 |
| | 200 | | | 0 | 25 |

In Table 3, the degree of resistance to the superoxide propagator is represented by the relative values of the growth to the control.

EXPERIMENT 3

The activity of the superoxide dismutase of each test strain was determined according to the Nitroblue tetrazolium method (V. Ponti et al, *Chem.-Biol. Interaction*, 23, 281-291 (1978)).

Thus, twenty ml portions of an aqueous medium, pH 7.0, which contain (per deciliter) 0.5 g yeast extract, 1.0 g peptone, 0.5 g bouillion and 0.5 g NaCl, were poured into 500 ml flasks and heated for sterilization.

One loopful inoculm of each of the microorganisms listed in Table 4 below was transferred into each batch of the culture medium, and cultivation was carried out at 30° C. for 24 hours with shaking. The microbial cells which accumulated in the culture broth were collected by centrifugation and washed twice with 0.1 M phosphate buffer, pH 7.0. The cells were then suspended in 20 ml of the same buffer, and the cell suspensions were subjected to sonication for 5 minutes (with cooling) to rupture the cells, and then centrifuged at 10,000 rpm for 10 minutes to obtain supernatant solutions.

0.1 ml of each supernatant solution (sample solution) thus obtained was mixed with 2.4 ml of 0.05 M sodium carbonate buffer, pH 10.2; 0.1 ml nM Xanthine; 0.1 ml of 3 mM EDTA; 0.1 ml of 0.15% bovine albumin; and 0.1 ml of 0.75 mM nitro blue tetrazolium. Then the mixture was kept at 25° C. for 10 minutes to activate enzyme activity. After the preincubation as above, 0.1 ml of Xanthin oxidase solution, which is 2 M ammonium sulfate solution containing $2.1 \times 10^{-7}$ M Xanthine oxidase, was added to the preincubated mixture solution. Then the solution was allowed to stand at 25° C. for 10 minutes followed by addition of 0.1 ml of 6 mM $CuCl_2$ to stop the reaction. Thereafter, the optical density of the reaction solution at 560 nm was determined. As the control a similar reaction was performed using distilled water instead of the sample solution.

1.0 unit of the enzyme activity of the superoxide dismutase is defined as the enzyme activity which inhibits 50% of the Xanthine oxidase reaction performed under the condition as above.

The enzyme activity of the superoxide dismutase thus determined are shown in the following Table 4, in which the activity is represented by the relative value of the enzyme activity to the control.

TABLE 4

| Superoxide dismutase activity | |
|---|---|
| Strain | (%) |
| ATCC 13869 | 100 |
| AJ 11796 | 151 |
| ATCC 13032 | 100 |
| AJ 11801 | 205 |

The mutants are cultured aerobically in a conventional culture medium containing carbon sources, nitrogen sources and inorganic ions, and minor nutrients when required.

As the carbon sources, saccharides such as glucose, sucrose, molasses and hydrolyzed starch, organic acids such as acetic acid and propionic acid, and alcohols such as ethanol can be used preferably. Nitrogen sources are, for example, ammonium sulfate, gaseous ammonia and urea. As the inorganic ions, $K^+$, $Na^+$, $Ca^{++}$, $Fe^{++}$, $Mn^{++}$, $Mg^{++}$, $Zn^{++}$, $SO_4^{--}$, $Cl^-$ and $PO_4^{--}$ are added to the culture medium when required.

When a carbon source which does not contain biotin, such as hydrolyzed starch, is employed, biotin is added to the culture medium. Biotin concentratin in the medium has to be controlled to less than the maximum amount allowable for the growth of the mutant.

On the other hand, when there is used a raw carbon source such as cane molasses containing more biotin than the proper amount for the growth of the mutant, an anti-biotin agent such as Penicillin, a higher fatty acid, or a surface-active agent is added to the medium.

Cultivation is normally carried out under aerobic conditions for from 20 to 80 hours at a temperature ranging from 30 to 38° C. The pH of the culture medium is controlled between 6.0 to 8.0 with the addition of an organic or inorganic acid or an alkali. For this purpose, urea, $CaCO_3$ or gaseous ammonia is preferably used.

L-Glutamic acid which accumulates in the culture broth can be recovered by any conventional recovery method.

Having now generally described this invention, the same will be better understood by reference to certain specific examples which are included herein for purposes of illustration only and are not intended to be limiting of the invention or any embodiment thereof, unless specified.

EXAMPLE 1

Twenty-milliliter portions of an aqueous culture medium, of which the composition was as given in Table 5, were poured into 500 ml flasks and heated at 115° C. for 10 minutes for sterilization.

TABLE 5

| Composition of culture medium | | | |
|---|---|---|---|
| Component | Conc. | Component | Conc. |
| Glucose | 36 mg/ml | $MnSO_4.4H_2O$ | 8 μg/ml |
| Urea | 2 mg/ml | Thiamine.HCl | 10 μg/dl |
| $KH_2PO_4$ | 1 mg/ml | Biotin | 0.25 μg/l |
| $MgSO_4.7H_2O$ | 0.4 mg/ml | Soy Protein hydrolyzed | 5 μl/ml |
| $FeSO_4.7H_2O$ | 10 μg/ml | | |

Each strain to be tested, as listed in Table 5 and grown on bouillon agar medium, was inoculated into the medium and cultured at 31.5° C. with shaking. During the cultivation, a small amount of an aqueous solution containing 450 mg/ml of urea was fed into the medium so as to maintain the pH of the culture medium in the range from 6.5 to 8.0. After 30 hours of cultivation, the amount of L-glutamic acid which had accumulated in the culture broth was determined and the results obtained are shown in Table 6.

TABLE 6

| Strain No. | L-glutamic acid accumulated (g/l) | Yield (%) |
|---|---|---|
| ATCC 13869 | 16.2 | 45.0 |
| AJ 11896 (FERM BP-251) | 18.5 | 51.4 |
| ATCC 13032 | 15.5 | 43.0 |
| AJ 11801 (FERM BP-250) | 17.7 | 49.2 |

EXAMPLE 2

A culture medium (pH 7.0) containing, per milliliter, 100 mg sugar (cane molasses), 1 mg $KH_2PO_4$, 1 μg thiamine HCl, 1 mg $MgSO_4$ and 1 mg $MgSO_4.7H_2O$ was prepared. Thirty-ml portions of the medium were poured into 500-ml flasks and heated for sterilization. Then each strain to be tested, as listed in Table 7, was inoculated into the medium and cultured at 31.5° C. with shaking. During the cultivation, a small amount of an aqueous solution of urea (400 mg/ml) was fed into the medium so as to maintain the pH of the medium in the range from 6.5 to 8.0. Polyethylene sorbitan monopalmitate was added to the medium when the optical density of a 26-times diluted solution of the culture medium came up to 0.300.

After 36 hours of cultivation, the amount of L-glutamic acid which had accumulated in the culture broth was determined. The results are as shown in Table 7.

TABLE 7

| Strain No. | L-glutamic acid accumulated (g/l) | Yield (%) |
|---|---|---|
| ATCC 13869 | 49.5 | 49.5 |
| AJ 11796 (FERM BP-251) | 52.5 | 52.5 |
| ATCC 13032 | 49.3 | 49.3 |
| AJ 11801 (FERM BP-250) | 51.5 | 51.5 |

The yield of L-glutamic acid can be increased by more than 2.0 percent by using the mutant of the present invention, and the increase in yield can produce a good increase in profit because more than 600,000 tons of L-glutamic acid have been produced by fermentation processes.

The invention now being fully described, it will be apparent to one of ordinary skill in the art that many changes and modifications can be made thereto without departing from the spirit or scope of the invention as set forth herein.

What is claimed as new and desired to be secured by Letters of the United States is:

1. A process for producing L-glutamic acid by fermentation which comprises:
   culturing aerobically in a culture medium a mutant microorganism of the genus Brevibacterium or Corynebacterium which is capable of surviving in a culture medium containing 2.0 μg/ml of daunomycin or 200 μg/ml of methyl viologen and which is capable of producing L-glutamic acid in the culture medium; and
   recovering the L-glutamic acid from the culture medium.

2. A process according to claim 1, wherein the mutant is capable of surviving in a culture medium containing daunomycin at a concentration of 3 mg/ml.

3. A method of increasing the glutamic acid producing ability of a bacterium of the genus Brevibacterium or Corynebacterium, which comprises:
   adding an inoculum of said bacterium to a series of culture media containing different concentration of a superoxide propagator;
   determining a concentration of superoxide propagator sufficient to prevent growth of said bacterium in said culture medium;
   mutating a culture of said bacterium;
   adding an inoculum of said mutated culture to a culture medium containing said determined concentration of superoxide propagator and
   selecting surviving bacteria from said medium.

4. A process according to claim 9, wherein the mutant belongs to the species Brevibacterium lactofermentum or Corynebacterium glutamicum.

5. A process according to claim 9, wherein the mutant in Brevibacterium lactofermentum FERM BP-251 or Corynebacterium glutamicum FERM BP-250.

6. A process according to claim 2, wherein the mutant belongs to the species Brevibacterium lactofermentum or Corynebacterium glutamicum.

7. A process according to claim 2, wherein the mutant is Brevibacterium lactofermentum FERM BP-251 or Corynebacterium glutamicum FERM BP-250.

8. The method of claim 2, wherein the superoxide propagator is daunomycin or methylviologen.

9. The method of claim 3, wherein the superoxide propagator is 2 mg/ml daunomycin or 200 mg/ml methylviologen.

* * * * *